United States Patent [19]

Agrawal

[11] Patent Number: 5,026,688

[45] Date of Patent: Jun. 25, 1991

[54] NOVEL AZT ANALOGS

[75] Inventor: Krishna Agrawal, New Orleans, La.

[73] Assignee: Administrators of the Tulane Educational Fund, New Orleans, La.

[21] Appl. No.: 265,201

[22] Filed: Oct. 31, 1988

[51] Int. Cl.$^5$ .............................................. A61K 31/70
[52] U.S. Cl. ..................................... 514/50; 514/885; 536/23
[58] Field of Search ...................... 536/23, 24; 514/49, 514/50

[56] References Cited

PUBLICATIONS

Weiss et al., *Molecular Biology of Tumor Viruses*, 2nd Edition, Cold Spring Harbor Laboratory, (1984), pp. 46–51.

Torrence et al. "AIDS dementia: synthesis and properties of a derivative of 3′-azido-3′-deoxythymidine (AZT) that may become locked in the central nervous system." FEBS Letters, 1988 (Jul.), vol. 234(1), 135–140.

*Primary Examiner*—John W. Rollins
*Assistant Examiner*—James O. Wilson
*Attorney, Agent, or Firm*—Pennie & Edmonds

[57] ABSTRACT

The present invention relates to novel ester derivatives of the anti-retroviral compound AZT, and compositions containing same. It also relates to methods of treatment of retroviral infections comprising administration of said compounds to individuals in need of such treatment.

28 Claims, 7 Drawing Sheets

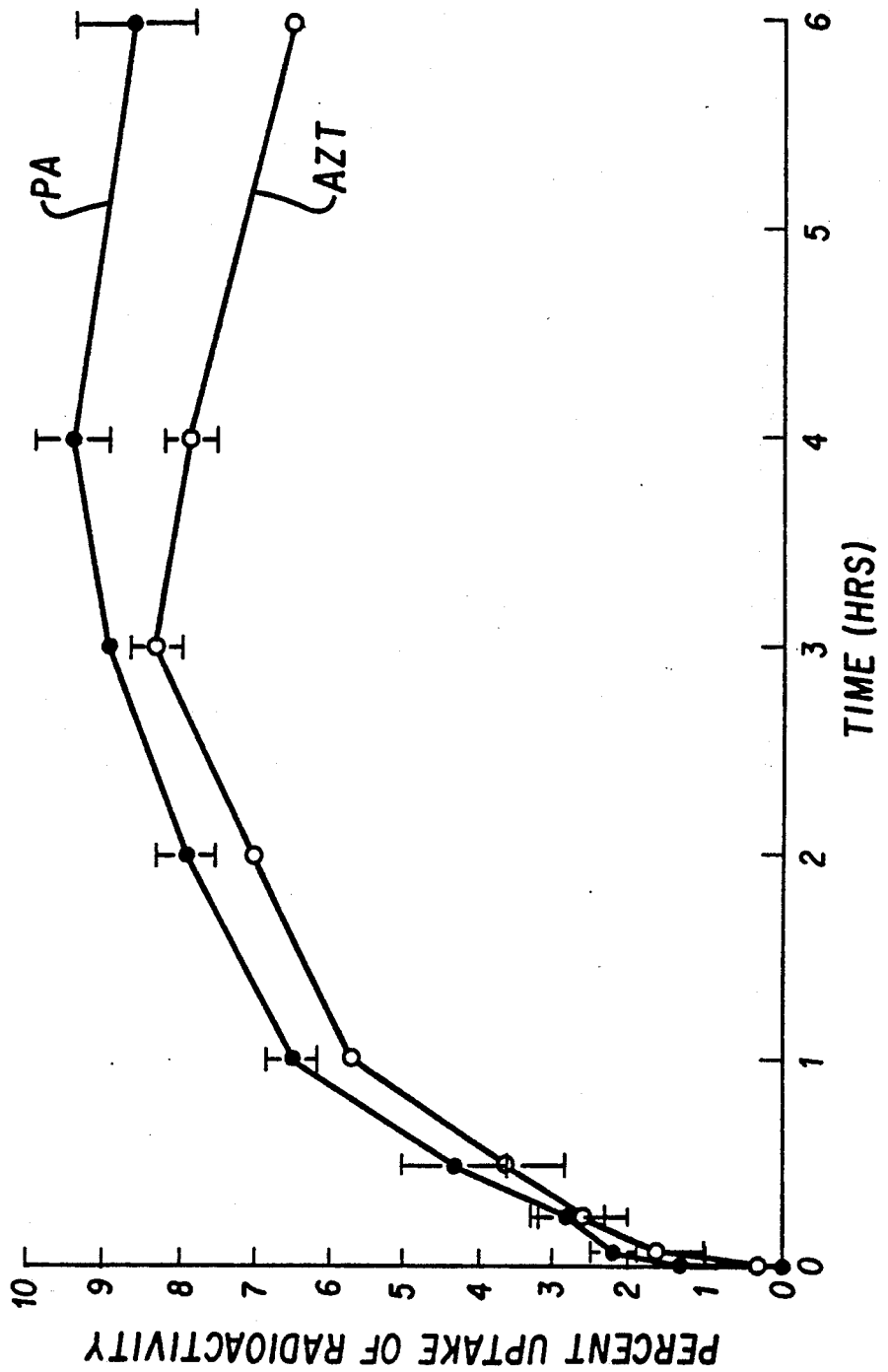

NOVEL AZT ANALOGS

TABLE OF CONTENTS

1. Introduction
2. Background of the Invention
2.1 Acquired Immune Deficiency Syndrome
2.2 AIDS Immunotherapy
2.3 AIDS Chemotherapy
2.4 AZT Alternative
3. Summary of the Invention
4. Brief Description of the Figures
5. Detailed Description of the Invention
5.1 DP-AZT
    5.1.1. Synthesis
    5.1.2. Biological Activity
        5.1.2.1. Permeability and Cellular Uptake
        5.1.2.2. Conversion of DP-AZT to AZT
        5.1.2.3. Bone Marrow Toxicity
        5.1.2.4. Antiviral Activity
5.2. Other AZT Ester Analogues
    5.2.1. Retinoic Acid Analogue
    5.2.2. Amino Acid Analogues
    5.2.3. Piperazine Analogue
5.3. Therapeutic Use
6. Examples
6.1. Chemical Synthesis of DP-AZT
6.2. Biological Utility DP-AZT
    6.2.1. Cellular Uptake
    6.2.2. Hydrolysis of DP-AZT
    6.2.3. Hydrolysis of DP-AZT in Mouse Bone Marrow Cells
    6.2.4. Toxicity of Bone Marrow Cells
    6.2.5. Antiviral Activity

1. INTRODUCTION

The present invention relates to novel compounds useful in the treatment of AIDS and AIDS-related complex. Specifically the invention relates to novel analogues of the compound azidothymidine (AZT) and a method of treating AIDS using these compounds.

2. BACKGROUND OF THE INVENTION

2.1. ACQUIRED IMMUNE DEFICIENCY SYNDROME

Acquired immune deficiency syndrome (AIDS) has in recent years become a major focus of health related research in the United States, and similar attention is beginning to be devoted in other countries as well. The disease, which is caused by a retrovirus known as human immunodeficiency virus (HIV-1), has reached near-epidemic proportions in the U.S., and at the present time there is no known cure. AIDS in its most advanced stages is characterized generally by a suite of ailments which have typically been associated with individuals whose immune system has been compromised or actively suppressed by drug administration. Among these diseases which are infrequently observed in immunologically normal individuals is Kaposi's sarcoma, a rare form of skin cancer, and numerous opportunistic infections such as *Pneumocystis carinii* pneumonia, toxoplasmosis, histoplasmosis, cryptococcosis, and cytomegalovirus. Occasionally, infection may be associated with a debilitating condition referred to as AIDS-related complex (ARC) which is characterized by unexplained fevers, night sweats, chronic diarrhea, and wasting. Although the present understanding of the mode of action and ultimate effects of the virus are in no way complete, it is generally understood that the virus preferentially infects and destroys helper/inducer T lymphocytes, specifically those known as OKT4+ or T4 cells. These T4 cells are involved in orchestrating cell mediated immunity by influencing the activity of cytotoxic cells such as T8 lymphocytes and natural killer cells. T4 cells also influence the activity of monocytes and macrophages which engulf infected cells and foreign particles, and also produce cytokines. The decline in T4 cell populations can be observed relatively early in the progress of an HIV infection. The loss of these helper T cells severely impairs the body's ability to mount an immune response against the intracellular pathogens which ultimately give rise to the opportunistic infections which characterize this disease; however, deficiencies in nearly all aspects of the host defense system have been observed in patients with AIDS.

2.2. AIDS IMMUNOTHERAPY

As already noted, there is not yet any available cure for AIDS, and the disease is, at this time, almost inevitably fatal. The multitude of observed effects, many with different immunological bases, has made selection of a therapeutic regimen difficult at best. In an effort to remedy T-cell deficiency, administration of various thymic extracts have been suggested. A similar application has been proposed for T-cell growth factor. Interferon is also known to increase T-cell, macrophage and natural killer cell cytocidal activity; however, interferon also has the effect of inhibiting lymphoproliferative responses, and therefore may ultimately contribute to immunosuppressive activity as well. Isoprinosine, an antiviral agent, has also been thought to show some promise.

An alternate approach to correcting the immunodefect has been to attempt to manage the opportunistic infections which result from immunedeficiency. This approach is the basis for the proposed administration of lymphokines, which normally in vivo act as macrophage regulating factors in response to T-cell; therapeutic use of these substances could conceivably enhance the microbicidal activity of macrophages in the absence of T-cell activity. A similar utility has been suggested for muramyl dipeptide, which directly activates tumoricidal and virucidal activity of macrophages. A number of proteins characteristic of the HIV viral envelope have now been identified, thus giving rise to the hope that a protective subunit vaccine can ultimately be produced. Despite the theoretical potential of all the aforementioned therapies, however, none of them has yet been proven very successful or achieved widespread use for the treatment of AIDS victims.

2.3. AIDS CHEMOTHERAPY

A number of antiviral agents are currently in trial stages for use as an AIDS drug. Such compounds include dideoxycytidine, dideoxyadenosine, phosphonoformate, rifabutin, and rebaviran, all of which appear to have some type of antiviral activity. Interestingly, given the variety of possible immunotherapeutic and chemotherapeutic approaches to AIDS treatment, the only method of treatment which has, to date, been widely accepted as having demonstrated utility is administration of the compound 3'-azido-2',3'-dideoxythymidine, also known as azidothymidine, zidovudine, and, most commonly, as AZT. This substance is the only FDArecognized drug for AIDS treatment at this time. AZT, originally synthesized by Lin and Prusoff (*J. Med. Chem.* 21:109–112, 1978) is a nucleoside analogue having the following formula

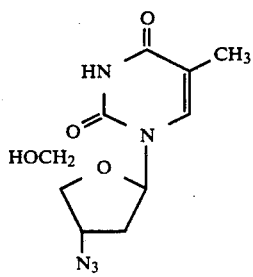

The compound as a triphosphate is a competitive inhibitor of reverse transcriptase, an enzyme critical to the replication of all retroviruses, including HIV. Unlike other viruses which use their own DNA to produce RNA in the host cell, retroviruses use revised transcriptase to exploit RNA as a template for the production of DNA by the host cell. Application of the drug AZT in vitro blocks the expression of the p24 gag protein of HIV, which in turn prevents the infectivity and cytopathic effect of the virus in vitro (Mitsuya et al., *PNAS, USA* 82:7096–7100, 1985). The unphosphorylated compound per se does not inhibit reverse transcriptase.

The observed in vitro effects of AZT inevitably led to the hope that the compound would also have an in vivo utility. Its effectiveness has in fact been borne out in clinical studies (Yarchoan et al., *Lancet I*, 575–580, 1986), and significant differences in mortality have been observed in individuals treated with AZT in comparison with individuals treated with placebos (Fischl et al. *N. Engl. J. Med.* 317:185–191, 1987). It has also been shown to delay the progression of the disease in many individuals with AIDS-related complex. (Fischl et al., ibid.) For this reason, it has become the most widely used treatment currently available to alleviate symptoms of AIDS.

The promising utility of AZT has been marred somewhat by adverse side effects which are observed in a large proportion of patients being treated with it. (Richman et al., *New Eng. J. Med.* 317:192–197, 1987) These ill effects are manifested in a number of different forms. The major adverse reactions associated with AZT administration were nausea, myalgia and insomnia. Hematological abnormalities were also observed, primarily in the form of anemia, leukopenia, and neutropenia. Of particular concern is bone marrow suppression, which has been observed in a substantial percentage of those treated. Reduction in the dosage level of AZT in order to limit the drug-related toxicity has been accompanied by antigenemia, recurrent symptoms of the disease, and decreased CD4 positive cells, all of which suggests a T-lymphocyte cytotoxicity (Jackson et al., *Ann. Intern. Med.* 108:175, 1988).

Another problem associated with the use of AZT is the observation that the concentration of the compound in the cerebral spinal fluid (CSF) is dose related, and is approximately 35–70% of the plasma concentration, at dosage levels of 2.5–5 mg/kg, respectively (Klecker et al., *Clin. Pharmacol. Ther.* 41:407, 1987). This indicates that there is a direct relationship between lower CSF/plasma ratios with lower doses, thus necessitating administration of higher doses of AZT in order to achieve an adequate antiviral concentration in CSF. Since central nervous system involvement has been recognized as an important component of HIV-infection, the possibility of reducing toxicity by reducing dosage levels is very limited. These difficulties have tainted somewhat the promise that AZT treatment holds for AIDS patients, and side effects may be so severe in some cases as to require some patients' withdrawal from treatment programs. Thus, the toxicity of the AZT compound ultimately limits its utility as an acceptable treatment for AIDS.

2.4. AZT ALTERNATIVE

The present invention now provides an equally effective and less toxic alternative to the use of AZT. The novel compounds developed in connection with the invention are ester analogues of azidothymidine which eliminate many of the undesirable properties associated with AZT. The new compounds are in fact pro-drugs of AZT; in other words, the compounds are eventually converted to AZT upon metabolism within the target cells. However, the drug as administered has improved physicochemical properties which enhance the transport into the CSF, and which may reduce the overall toxicity of the compounds to bone marrow and other cells.

The use of pro-drugs as a delivery system to achieve sustained delivery of drugs to the central nervous system is known in the art. Bodor et al., (*J. Med. Chem.* 26:313–318, 1983) describe the use of a dihydropyridine pyridinium salt-type redox system for the brain-specific delivery of phenylethylamine. However, at least some of the present compounds achieve not only enhanced CSF transport but also exhibit a higher level of transport into other cells (e.g., peripheral blood lymphocytes), a significantly reduced bone marrow toxicity, and perhaps most surprisingly, an apparently superior antiviral activity when compared with AZT. The conjugation with certain esters to AZT therefore has the unexpected effect of substantially altering the activity of AZT in a highly favorable manner, so that the clinical potential of the thus-formed novel compounds is enhanced over AZT.

3. SUMMARY OF THE INVENTION

The present invention provides novel analogues of the known anti-retroviral compound (AZT); specifically the novel compounds are ester derivatives of AZT, which compounds have the formula:

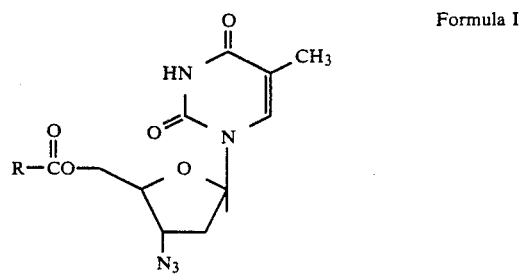

Formula I wherein R is selected from the group consisting of

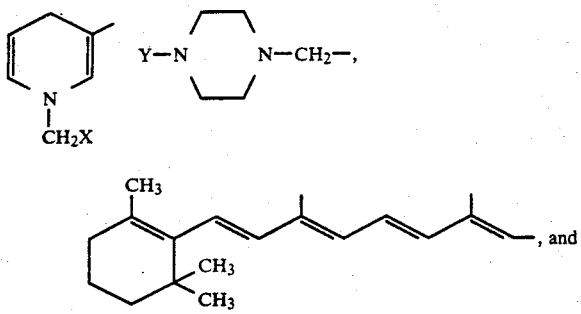

wherein X is hydrogen, carboxyl, $C_1$-$C_6$ alkyl, or benzyl; and Y is $C_1$-$C_6$ alkyl, $C_6$-$C_{10}$ aryl, or hydrogen.

The compounds are pro-drugs which are converted into AZT after transport into the target cells. The novel compounds and pharmaceutical compositions containing them, provide increased uptake by the cells of the central nervous system, decreased toxicity to bone marrow cells, and increased effectiveness against the HIV-1 virus. The invention also provides a second novel compound having the formula:

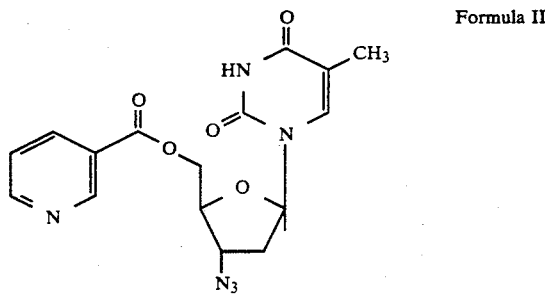

Formula II which is useful as an intermediate in the preparation of certain of the pro-drugs of the invention.

Also provided is a method of treatment of retroviral infection, particularly AIDS and ARC, which comprises administering to an infected individual an effective amount of a compound of Formula I, in combination with a pharmaceutically acceptable carrier.

4. BRIEF DESCRIPTION OF THE FIGURES

FIG. 8 shows the relative uptake of AZT and a phenylalanine AZT analogue by peripheral blood lymphocytes.

5. DETAILED DESCRIPTION OF THE INVENTION

The present compounds and method of use are based in principle on the utilization of esters of the biologically active compound AZT as prodrugs in an attempt to increase the uptake of the prodrug by the cells and thus to in turn increase the amount of AZT ultimately yielded in the cells upon hydrolysis. The linking of ester derivatives to the active AZT compound appears to enhance the permeability of AZT, and in some cases may have further beneficial effects with respect to toxicity and antiviral activity.

5.1. DP-AZT

The utility of the compound 5,-[(1,4-dihydro-1-methyl-3-pyridinylcarbonyl)oxy] -3,-azido-2',3'dideoxythymidine (DP-AZT) is based on utilization of a redox chemical drug delivery system of a dihydropyridine and a pyridinium salt. The linking of the biologically active compound AZT to a lipoidal dihydropyridine carrier appears to enhance the permeability of the active compound, and presumably permit it to cross the blood-brain barrier. The oxidation of the carrier in vivo to the ionic pyridinium salt prevents its elimination from the central nervous system, and subsequent hydrolysis of the quaternary carrier linkage provides sustained delivery of the parent drug.

5.1.1. SYNTHESIS

Figure 1:
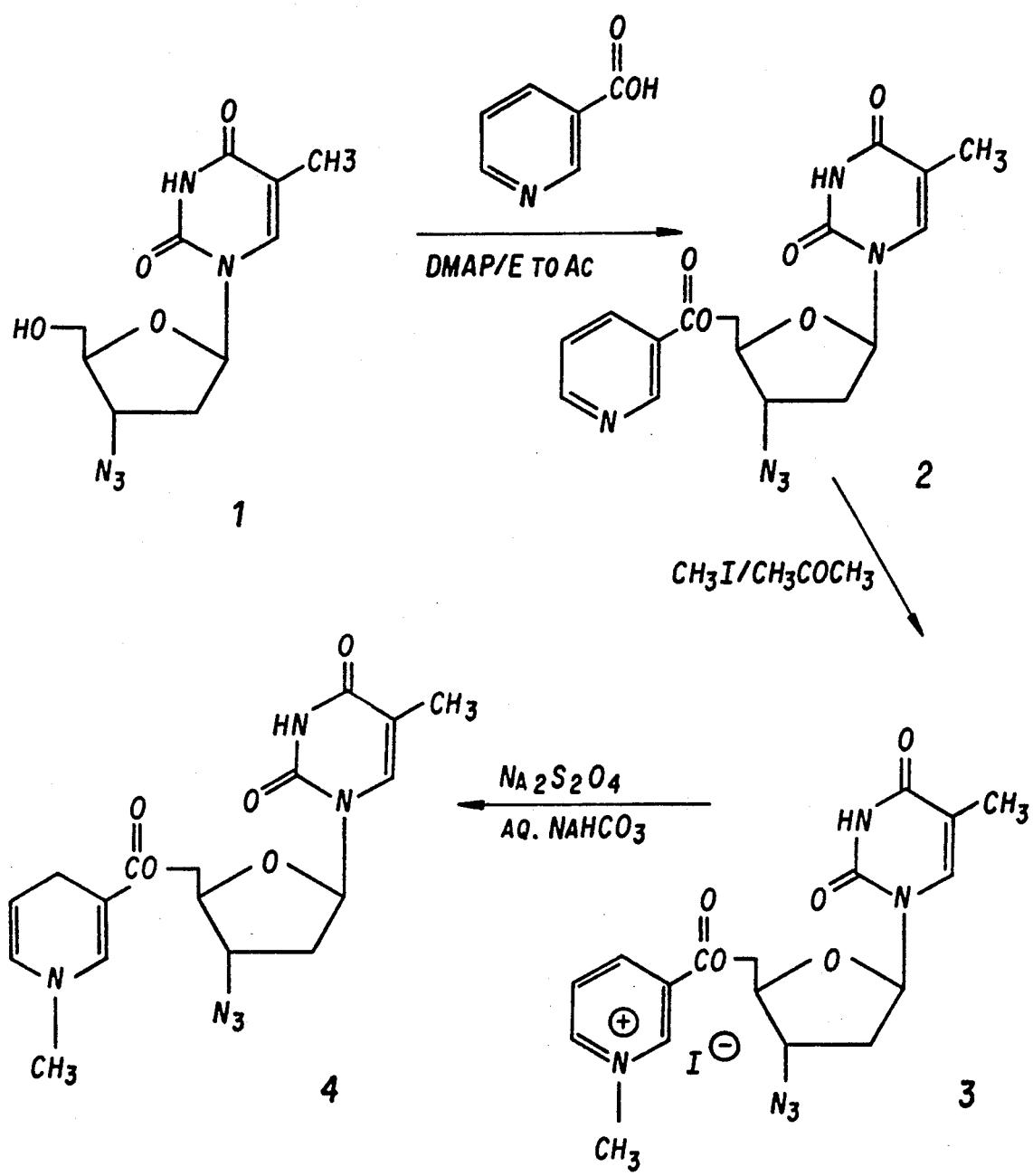
FIG. 1 shows a schematic representation of DP-AZT synthesis.

The general pattern of synthesis of DP-AZT is outlined in FIG. 1. Treatment of 3,-azido-2',3'-dideoxythymidine in the presence of DCC and 4-dimethyl amino pyridine in ethyl acetate yield the nicotinyl ester. The ester is then quarternized by refluxing it in acetone with methyl iodide. The compound (2) so produced is hygroscopic in nature, and is therefore directly reduced with sodium, dithionite and aqueous sodium bicarbonate to yield DP-AZT (3) The structure of this compound has been verified by UV, IR, NMR and elemental analysis. DP-AZT is a stable compound which does not undergo air oxidation during crystallization and drying. Attempted chemical oxidation of DP-AZT with hydrogen peroxide or sodium nitrate solution resulted in hydrolysis of the ester producing AZT. In addition to DP-AZT, other derivatives at the N-methyl site in particular can also be prepared.

5.1.2. BIOLOGICAL ACTIVITY

5.1.2.1. PERMEABILITY AND CELLULAR UPTAKE

Figure 2A:
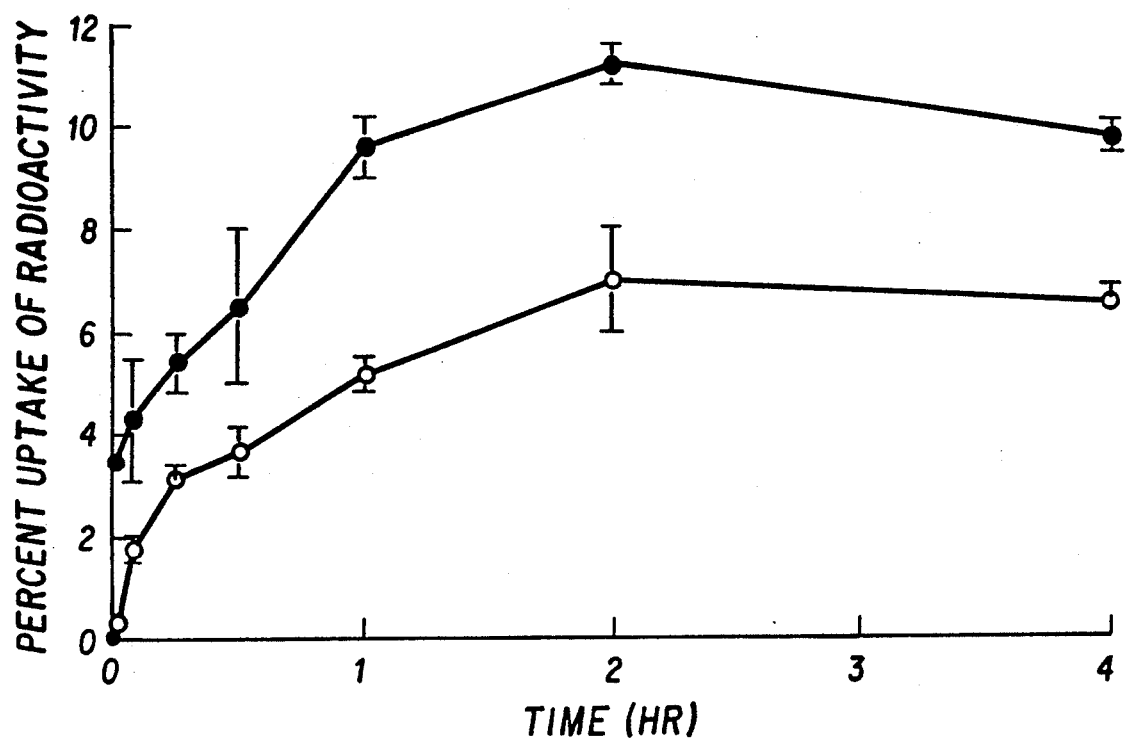
FIG. 2 shows the relative uptake of AZT (o-o) and DP-AZT(●-●)by (A) H9 (lymphoblastoid) cells and (B) peripheral blood lymphocytes.
Figure 2B:
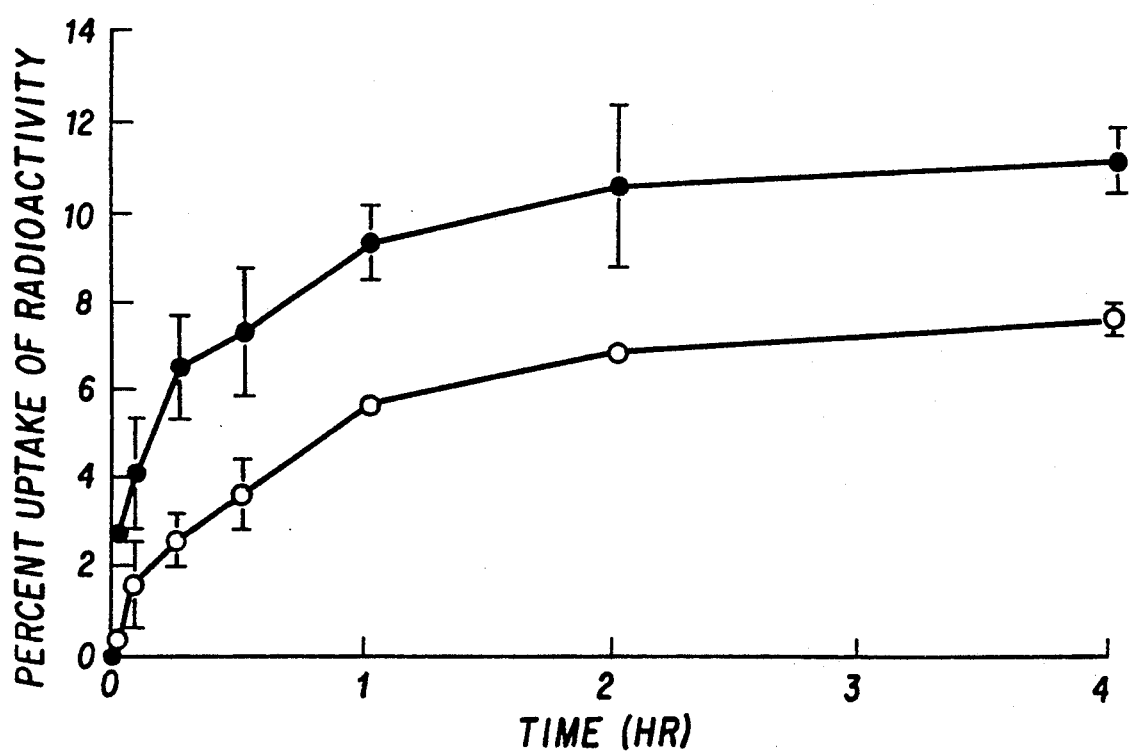

One of the primary problems with the use of AZT is its resulting relatively low concentrations in the central nervous system, and its very short half-life in plasma, necessitating higher dosage levels to achieve adequate antiviral concentrations. DP-AZT was therefore tested to determine if the problem of rapid elimination and inadequate permeability could be overcome. The extent of cell membrane permeability of DP-AZT relative to AZT was assessed by comparing their uptake in H-9 cells (an OKT4+ T-cell line that is permissive to HIV replication, but partially resistant to its cytopathic effects) and peripheral blood lymphocytes (PBL). At a clinically achievable level of 5 μM AZT, the uptake of [3H]-AZT and DP-[3H]-AZT was linear for one hour and reached maximum intracellular concentration at 2 hours (FIG. 2). The uptake of DP-[3H]-AZT was significantly higher than that of [³H]-AZT, achieving at least 50% higher intracellular concentration, in both H-9 and PBL cell lines.

5.1.2.2. CONVERSION OF DP-AZT TO AZT

To determine if peripheral blood lymphocytes (PBL) are capable of generating free AZT by intracellular hydrolysis of DP-AZT, a radiflow detection attached to an HPLC system were used to demonstrate the formation of AZT as a function of time. These results are shown in FIG. 3. Incubation of 500 μM DP-[³H]-AZT with $5 \times 10^5$ PBL followed by extraction of radioactivity and detection of the formation of [³H]-AZT indicated complete hydrolysis of the pro-drug within four hours. The results suggest that PBL can enzymatically hydrolyze the novel compounds to produce AZT containing an unsubstituted 5-OH function required for AZT, the real inhibitor of reverse transcriptase. In contrast, bone marrow cells were able to hydrolyze only 50% of the pro-drug at the end of 4 hours of incubation. This observation suggests that the hydrolytic enzymes in bone marrow cells do not possess activity similar to that of PBL, and this may be instrumental in reducing bone marrow toxicity for DP-AZT. DP-AZT was also not hydrolyzed by human plasma in vitro up to 4 hours in incubation, indicating the pro-drug is relatively stable in plasma. However, DP-AZT was hydrolyzed by rat-liver microsomes (FIG. 4) in a manner similar to that observed in PBL.

5.1.2.3. BONE MARROW TOXICITY

Figure 5:
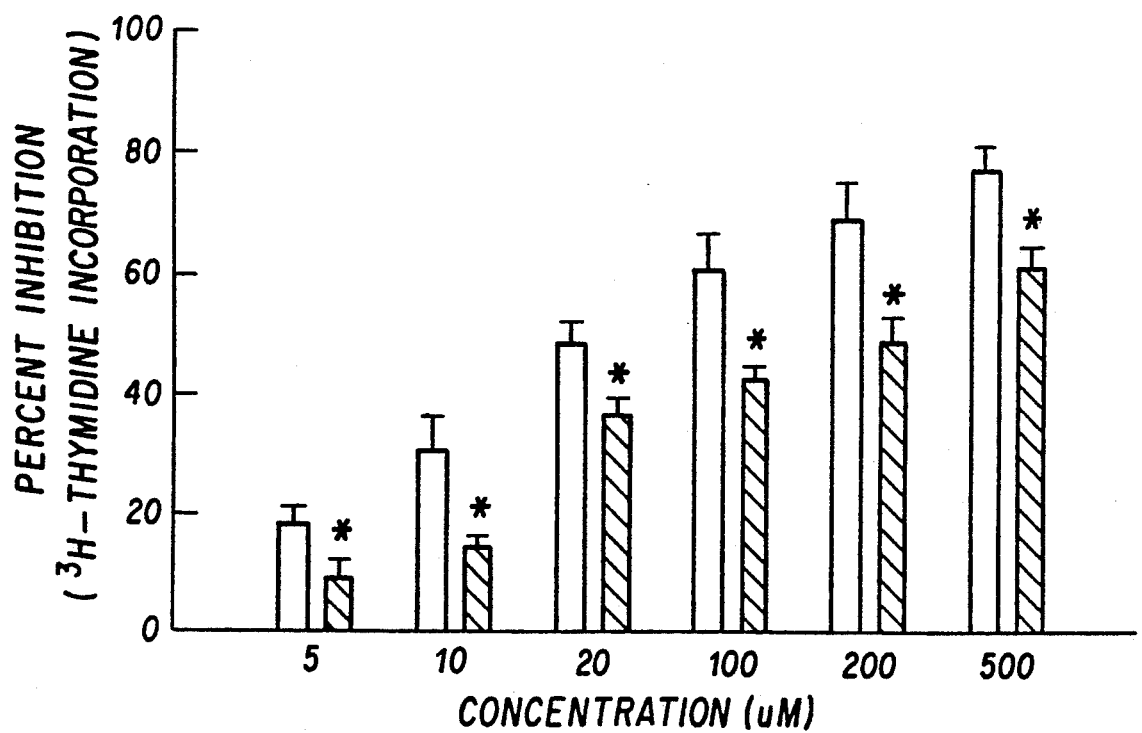
FIG. 5 shows the relative toxicity of AZT (open bar) and DP-AZT (solid bar) on mouse bone marrow cells.

Murine bone marrow cells were exposed to various concentrations of AZT and DP-AZT for a period of 60 hours, followed by [³H]-thymidine pulse for 12 hours. The percent inhibition of [³H]-thymidine uptake was used as an indication of bone marrow toxicity (FIG. 5). At clinically relevant concentrations of 5 and 10 μM of each agent, DP-AZT was significantly less toxic than AZT, resulting in respectively, 44% and 59% less inhibition of [³H]-thymidine incorporation into bone marrow cells. These data indicate that DP-AZT is comparatively less toxic to bone marrow cells than AZT, this decrease in cytotoxicity possibly being related to decreased hydrolysis of the pro-drug in bone marrow cells, as noted above.

5.1.2.4. ANTIVIRAL ACTIVITY

The antiviral activity of both DP-AZT and AZT was compared in vitro in PBL obtained from HIV seronegative donors. The concentration of virus-specific p24 antigen in the culture, and, therefore the ability of each drug to inhibit HIV replication was measured by their ability to inhibit production of the p24 antigen. These results are presented in Table I, infra.

These data show that DP-AZT at a 0.5 μM concentration had significantly greater efficacy against HIV-1 than AZT had. The 99% inhibition by DP-AZT at 0.5 μM was similar to that achieved with 5 μM AZT, suggesting that DP-AZT has superior antiviral activity in this system.

5.2. OTHER AZT ESTER ANALOGUES

Other AZT ester analogues have also been prepared, each showing enhanced cellular uptake relative to AZT.

5.2.1. RETINOIC ACID ANALOGUE

Recent reports (Watson et al., *Life Sci* 43:xiii–xviii, 1988) indicated that Vitamin A administration to retrovirally infected mice increased numbers of activated macrophages and decreased death rate. Retinoic acid has also been shown to inhibit HIV replication somewhat (Yamamoto et al., *AIDS Res.* 2:S183–S189, 1986). In another embodiment of the invention, therefore, a retinoic acid ester of AZT was prepared. The synthetic method followed was:

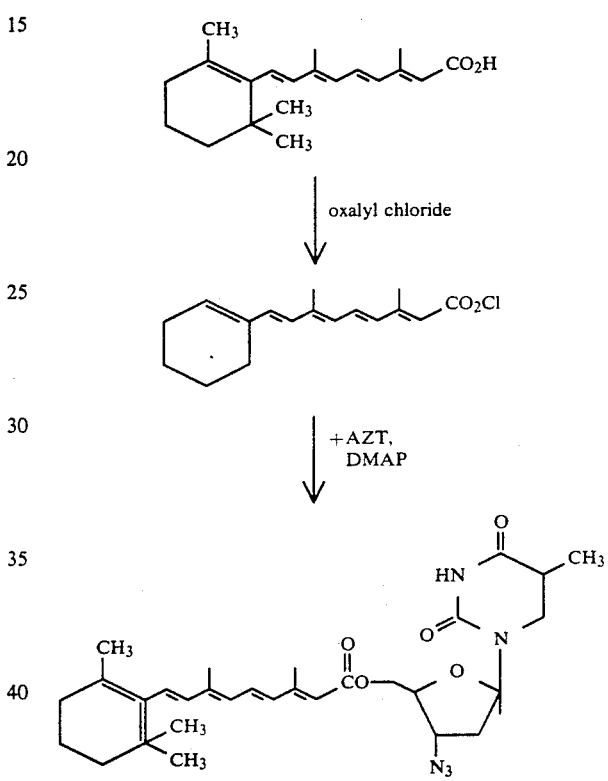

This compound was evaluated for its ability to be taken up by H9 cells. The results shown in FIG. 7 indicate a substantial improvement over cellular uptake of AZT.

5.2.2. AMINO ACID ANALOGUES

Amino acid transport systems have been previously characterized with respect to L-phenylalanine mustard (Vistica and Schnotte, *Biochem. Biophys. Res. Comm.* 90:247–252, 1979). In another embodiment of the present invention, attempts were made to create amino acid analogues of AZT. The synthetic pathway for two such analogues is as follows:

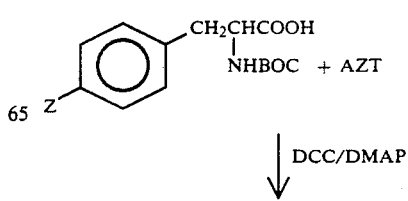

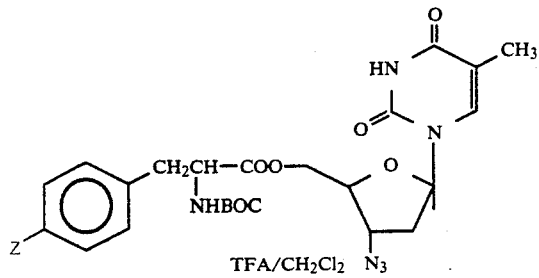

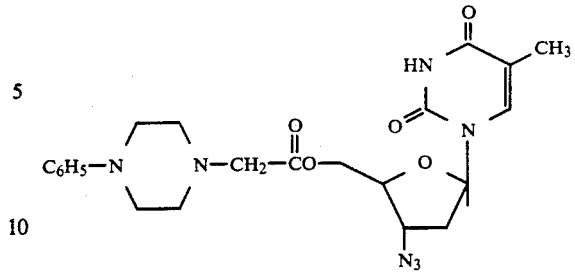

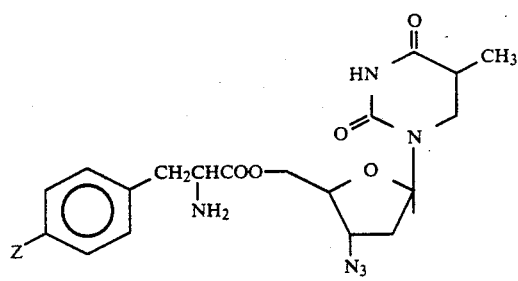

where Z is OH or H.

Figure 6:
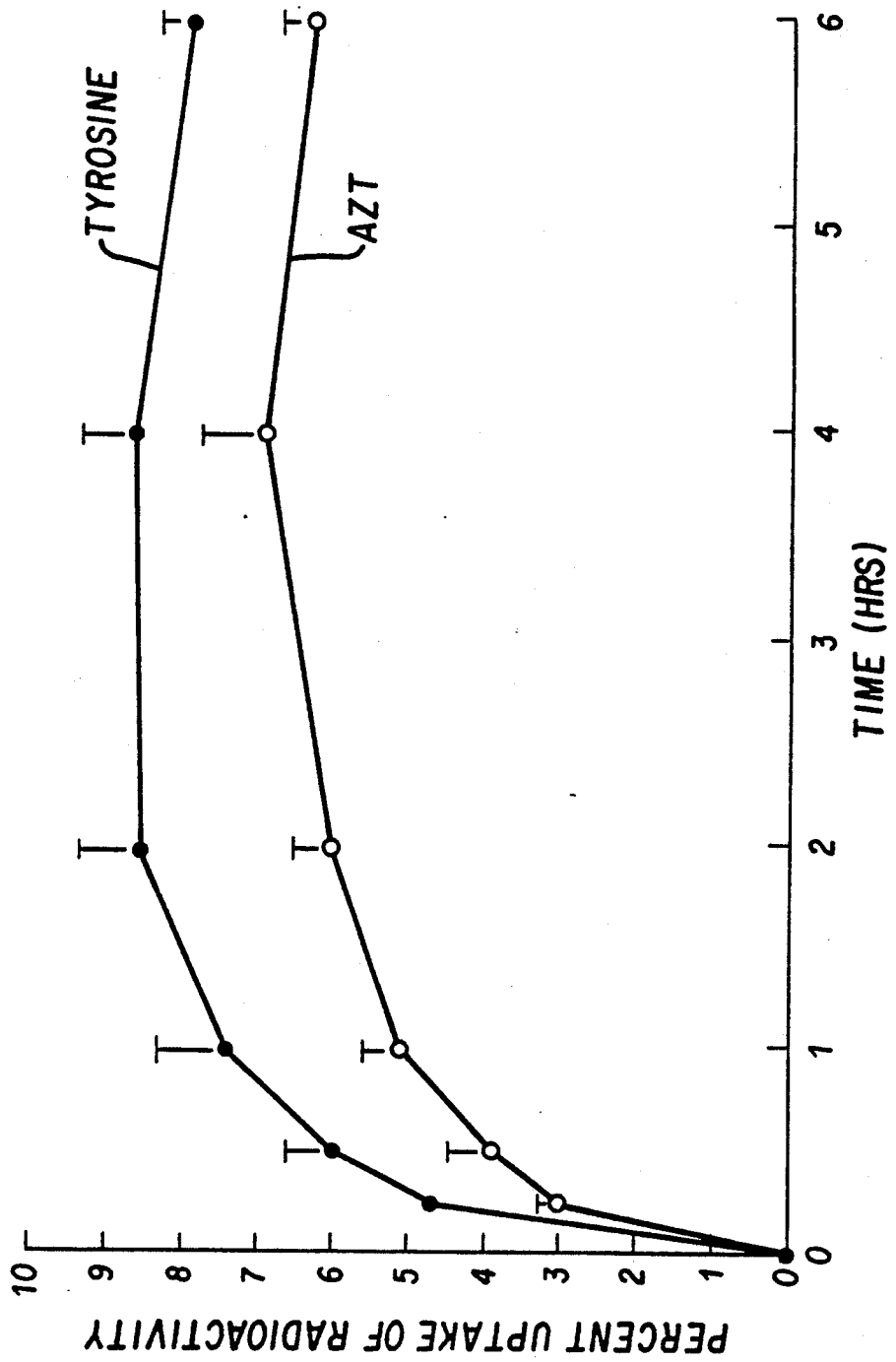
FIG. 6 shows the relative uptake of AZT and a tyrosine AZT analogue by H9 cells.

These two analogues, with phenylalanine and tyrosine as amino acid, were tested for their ability to be taken up by PBL and H9 cells, respectively, relative to AZT. The results, shown in FIGS. 6 and 8, indicate that both amino acid analogues are improved over AZT with respect to cellular uptake. The synthetic route described above also may be used to create other amino acid analogues by simply substituting a different amino acid for phenylalanine or tyrosine in the procedure outlined. Another preferred analogue is one in which the amino acid is isoleucine, because of its lipophilicity. Also useful is a serine acid ester, as T-lymphocytes have been shown to possess serine esterases.

5.2.3. PIPERAZINE ANALOGUE

Figure 7:
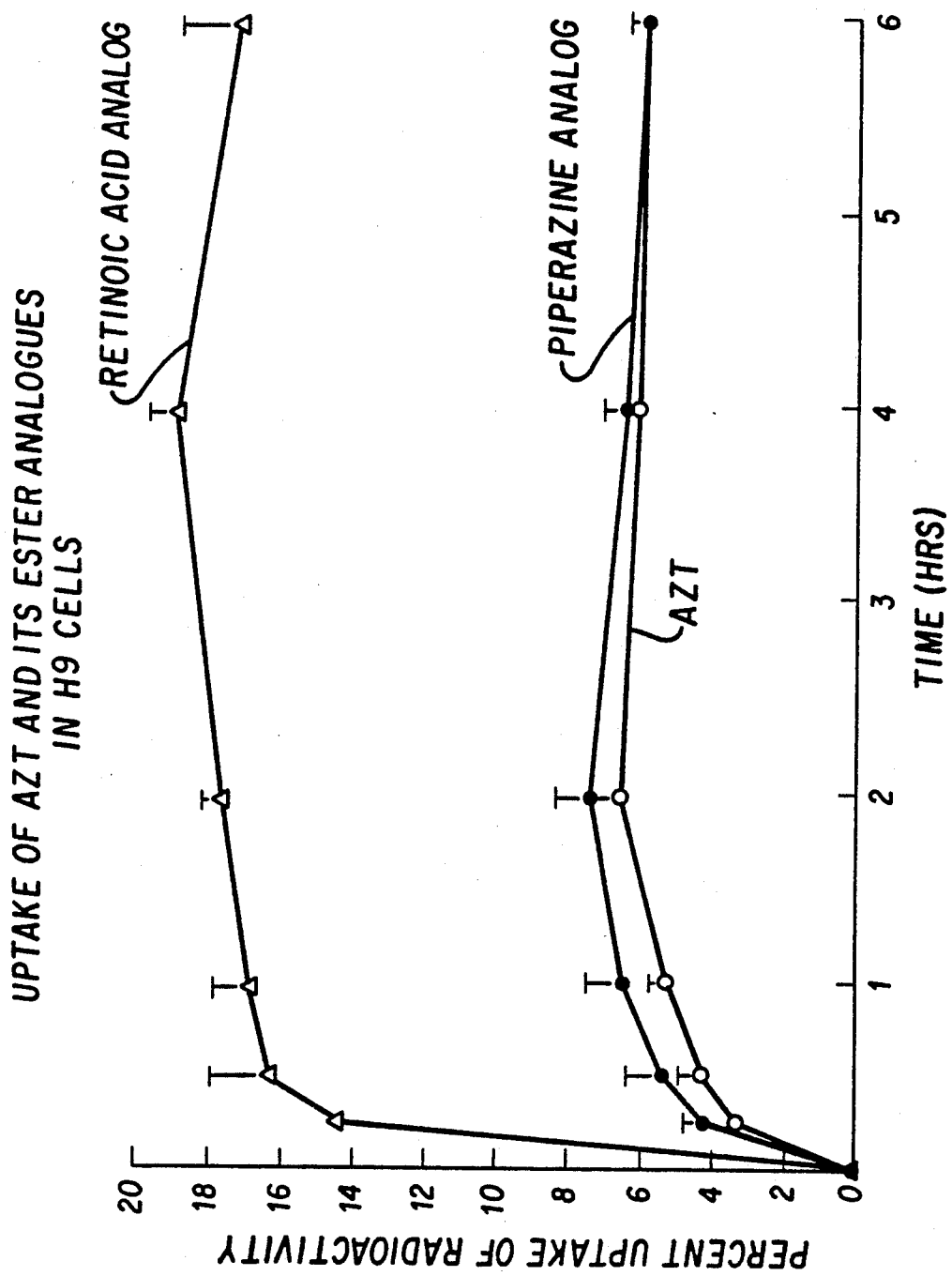
FIG. 7 shows the relative uptake of AZT and two ester analogues, a piperazine (Pip) and retinoic acid (RE) analogue by H9 cells.

Also synthesized in connection with the present invention is an N-phenylpiperazine analogue. It has been reported (Hansen and Hassan, *J. Med. Chem.* 30:29-34, 1987) that the brain reptake of I-alkyl-4-phenylpiperazines resulted in a brain/blood ratio of >20. In the present case, the linking of a phenylpiperazine moiety to AZT has resulted in an improved cellular uptake (FIG. 7). In addition, initial observations also indicate little or no toxicity of the piperazine derivatives to bone marrow cells. The synthetic route for preparation of the phenyl piperazine analogue is as follows:

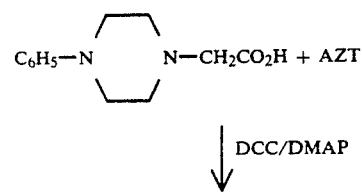

DCC/DMAP

Other alkyl and aryl analogues substituted in place of the phenyl group can be made by the above route using known starting materials.

5.3. THERAPEUTIC USE

The compounds of the present invention may be employed in much the same manner as AZT has been employed in the treatment of AIDS and ARC. These compounds may be used in the treatment of other retroviral infections, such as HIV-2 and -3, feline leukemia virus, feline sarcoma virus, Rous sarcoma virus, and avian leukosis virus.

The dosage levels of the compounds of the present invention are generally provided in amounts equimolar with the known dosage levels of AZT, although downward adjustments may be made to take into account the increased permeability of the present compounds. An example of one type of treatment program is oral administration of from 150-250 mg preferably about 200 mg, of the compound DP-AZT every 4 hours. The decrease in toxicity observed with the present compounds may permit a higher frequency of administration under circumstances which require it, however, so the foregoing regimen is simply provided as a guideline. Using the established regimens for AZT administration as a standard, it is well within the ability of the treating physician to vary the treatment program to provide equimolar amounts of the compound relative to AZT, and to vary administration depending upon the patient's needs and responses.

The compounds can also be administered parenterally, by solubilizing in dimethyl acetamide, with a dose in the range of about 100-200 mg.

Pharmaceutical compositions of the present invention may be formulated in accordance with the intended mode of administration of the drug. For oral administration, the present compound may be combined, in unit dosage form, with one or more pharmaceutically acceptable carriers to form, for example, capsules or tablets. Typical carriers include, but are not limited to, lactose, sucrose, starch, talc, magnesium stearate, crystalline cellulose, methyl cellulose, carboxymethyl cellulose, glycerin, sodium alginate or gum arabic. For parenteral administration, appropriate carriers are a mixture of dimethyl acetamide and physiological saline.

The following non-limiting examples are illustrative of the present invention.

6 EXAMPLES

6.1. CHEMICAL SYNTHESIS OF DP-AZT

In the synthetic protocol described below, the following techniques and apparatus were employed:

Melting points were determined on a Fisher-Johns melting point apparatus and are uncorrected. Silica gel plates (Merck F254) were used for thin-layer chromatography. The compounds were detected by visual examination under short and long-wave length UV light-IR spectra were recorded on Perkin-Elmer FTIR 1600 series spectrophotometer. Proton nuclear magnetic resonance spectra were recorded at 80 MHz on a varian FT-80A spectrophotometer using tetramethylsilane as the internal reference. UV spectra were recorded on a Beckman DB-G spectrophotometer. The radiopurity was determined by employing a Beckman (Model 340) HPLC system equipped with an on-line Flow-One Beta radioactive flow detector (Model CR, 3.5 ml cell type, Radiomatic Instruments). A reverse phase Econosphere C18 column (150× 4.6 mm, 5 µ) was used with aqueous 50% methanol as mobile phase. DP-AZT (3) was detected at 267 nm with a peak retention time of 9.4 min with a flow rate of 1 ml/min. For radioactivity detection, a simultaneous flow of scintillation cocktail (Flo-Scint II) was used at 6 ml/min. The elemental analyses were performed by Baron-Consulting Co., Orange, Conn., and are within ±0.4% of the calculated value when specified by symbols.

Numbers underlined in the following description refer to formulas on the scheme outlined in FIG. 1.

A. Preparation of 5'-(3-Pyridinylcarbonyloxy)-3,-azido-2',3'-dideoxythymidine (1).

DCC (2.12 g, 10.2 mmol) was added to a stirred solution consisting of 2.5 g (9.3 mmol) of AZT, 1.26 g (9.3 mmol) of 4-dimethylaminopyridine and 1.27 g (9.3 mmol) of nicotinic acid in ethyl acetate (150 ml) under anhydrous conditions. The progress of the reaction was monitored by TLC. After the completion of the reaction (~36-40 h), the separated DCU was filtered off. The filtrate was evaporated to dryness under reduced pressure using rotary evaporator and the residue was stirred with a 1:1 mixture of ethylacetate: ether (50 ml). The solid obtained was washed with ethyl acetate (5 ml) to give 2.9 g of crude 1 as white solid. This material was crystallized from ethyl acetate to give 2.12 g (60.9%) of 1 as white crystalline solid. In addition, 300 mg of 1 was further obtained by chromatography of the filtrate over silica gel using a mixture of hexane: ethyl acetate (1.5:8.5) as eluent to give a total of 2.42 g (69.5%) mp 137-9° C.; IR (KBr) 3390 (NH), 2100 ($N_3$), 1710 (C=O ester), 1680, 1650 (CONH); $^1$H NMR (CDCl$_3$) δ1.77 (3H, s, 5-Me), 2.56 (2H, t, H-2', J=8.75 Hz), 4.12–4.69 (4H, m, H3', H-4', H-5' & H-5''), 6.12 (1H, m, H-1'), 6.94–7.56 (2H, m, H-6 & C$_5$ pyridine H), 8.90 (1H, broad, C$_2$ pyridine H), 9.71 (1H, broad, NH, exchangeable with D$_2$O). Anal. (C$_{16}$H$_{16}$N$_6$O$_5$) C, H, N.

B. Preparation of 5'-[(1,4,-Dihydro-1-methyl-2pyridinylcarbonyl)oxy]-3'-azido-3'-dideoxythymidine (3).

A solution of 1.35 g (3.6 mmol) of 1 containing 3.9 g of iodomethane (21 mmol) in anhydrous acetone was stirred and refluxed for about 6 h. It was further stirred at ambient temperature overnight. The solvent was removed under reduced pressure and the residue was washed with absolute ethanol (2×25 ml) to give 1.7 g (91%) of 2 as a yellowish brown hygroscopic solid: IR (KBγ): cm$^{-1}$ 3320 (NH), 2080 (N$_3$), 1710 (C=O ester), 1680, 1650 (CONH); UV max (buffer pH 7.4) 224 nm (ε19136) and 264 nm (ε11996); $^1$H, NMR (DMSO-d$^6$) δ1.71 (3H, s, m, 5-Me), 2.60 (2H, m, H-2), 3.37–3.62 (1H, m, H-5'), 3.81 (3H, s, N-Me), 3.9–4.1 (3H, m, H-3', H-4, H-5'), 5.37–5.62 (1H, m, H-1'), 7.4 (1H, s, h-6), 8.09–8.37 (lH, m, C$_5$ pyridine H), 8.9-9.21 (2H, m, C4 & C6 pyridine H), 9.5 (lH, s, C2 pyridine H), 12.15 (lH, broad, NH, exchangeable with D$_2$O). This material was used directly in the next step.

To an ice cold suspension of 1.7 g (3.3 mmol) of crude 2 in 50 ml of deaerated water under nitrogen were added 2.7 g (15.5 mmol) of sodium dithionite and 1.3 g (15.5 mmol) of sodium bicarbonate and 50 ml of ethyl acetate. The mixture was stirred in ice for 1 h followed by further 2 h at ambient temperature. The ethyl acetate layer was separated and the aqueous layer was further extracted with ethyl acetate (3×50 ml). The combined ethyl acetate solution was washed with water (2×15 ml), dried over anhydrous sodium sulfate and evaporated to dryness to give a yellow solid which was crystallized two times from absolute ethanol to give 0.65 g (50.6%) of 3 as yellow solid: mp 132–5° C.; IR (KBδ, cm$^{-1}$) 3420 (NH), 2080 (N$_3$), 1710 (C=O ester), 1680, 1650 (CONH); UV max (Methanol) 217 nm (ε13521), 265 nm (ε116731), 359 nm (ε8035); $^1$H NMR (DMSO-d$^6$) δ1.75 (3H, s, 5-Me), 2.19–2.50 (2H, m, H-2'), 2.94 (3H, s, N-Me), 3.12–3.31 (2H, broad, C$_4$ pyridine H), 3.81–4.75 (4H, m, H-3', H-4', H-5' & H-5''), 5.62 (lH, m, C$_6$ pyridine H), 6.12 (lH, s, H-1'), 6.81 (lH, s, H-6), 7.31 (lH, broad, C$_2$ pyridine H), 11.12 (lH, broad, NH, exchangeable with D$_2$O). Anal. (C$_{17}$H$_{20}$N$_6$O$_5$) C, H, N.

C. Radiolabelled Synthesis.

[Methyl-$^3$H]DP-AZT was synthesized from 0.02 g of [methyl-$^3$H]AZT (specific activity 35.9 mCi/mmol) and 0.18 g of unlabelled AZT by following a similar sequence of reactions as depicted in Scheme I. The radiolabelled compound 3 (0.059 g) was purified by mixing it with 0.1 g of unlabelled 3 followed by crystallization from absolute ethanol. This procedure yielded 0.056 g of labelled 3 which was found to be 87.9% radiochemically pure by HPLC and had a specific activity of 0.46 mCi/mmol. Other labelled products were also made by using methyl-$^3$H AZT.

6.2. BIOLOGICAL UTILITY DP-AZT

6.2.1. CELLULAR UPTAKE

H9 cells, a lymphoblastoid line, were grown in RPMI 1640 medium supplemented with penicillin (100 U/ml), streptomycin (100 µg/ml), L-glutamine (2 mM) and 15% fetal bovine serum (FBS) at 37° C. in 5% CO$_2$, and 95% humidified air in an incubator.

A suspension of 5×10$^5$ cells (prewarmed at 37° in 100 µl) was pipetted into Eppendorf tubes and 100 µl of 5 µM DP-AZT was added to these cells and incubated at 37° C. for various time intervals (0–6 hr). The reaction was stopped by centrifugation at 13,000×g for 1 min. The cell free supernatant was discarded by aspiration and the cell pellet was washed with ice cold PBS to remove any traces of free radioactive drug. The cell pellet was resuspended in PBS and counted for radioactivity in a Tri-carb Packard liquid scintillation analyzer Model 1500 (Packard Instruments Co., Dowers Grove, Ill.) and the percentage of radioactivity was calculated. (All experiments were done in duplicate and repeated at least three times). These results are shown graphically in FIG. 2A.

PBL from HIV seronegative donors were also separated by standard Ficol-Hypaque gradient centrifugation. The lymphocytes were grown in RPMI 1640 supplemented with 15% heat-inactivated FBS, 100 U/ml penicillin, 100 µg/ml streptomycin and 2 µg/ml PHA.

The cells were incubated for 4 days at 37° C. and uptake studies were done according to the procedure described above for H9 cells. These results are shown graphically in FIG. 2B.

6.2.2. HYDROLYSIS OF DP-AZT

Figure 3A:
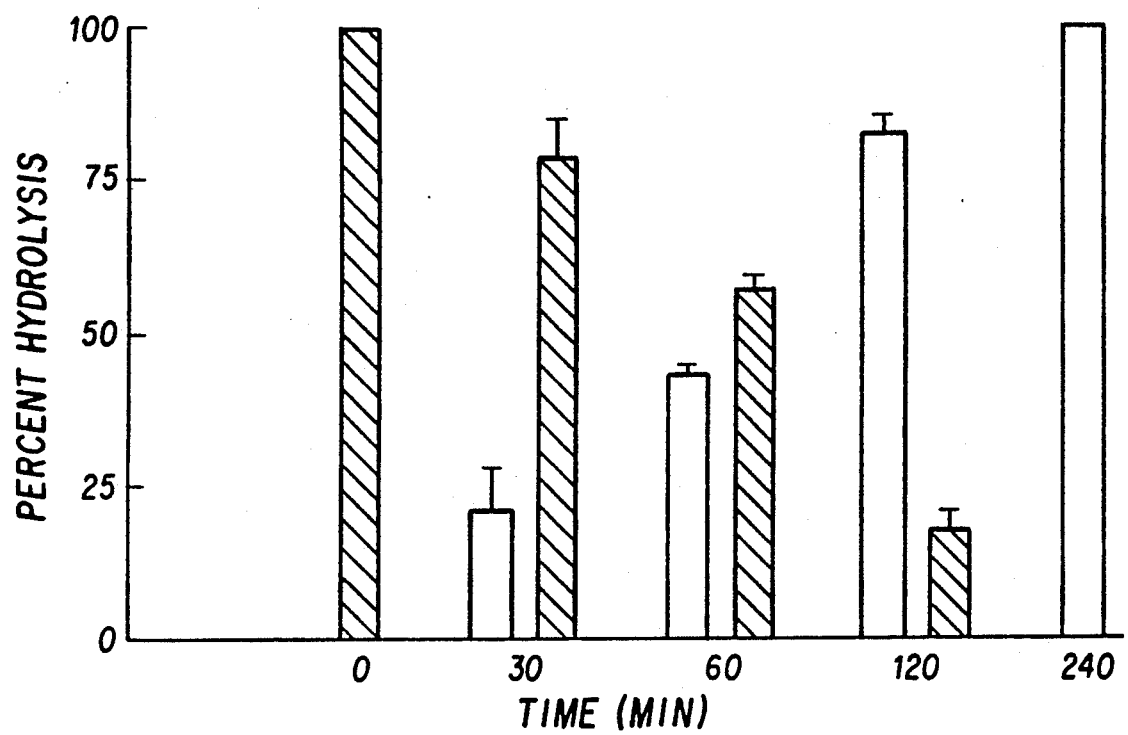
FIG. 3 shows the pattern of hydrolysis of DP-AZT in (A) peripheral blood lymphocytes and (B) mouse bone marrow cells.

Suspensions of $5 \times 10^5$ PBL (100 μl) in Eppendorf tubes were mixed with 100 μl of 500 μM DP-AZT and incubated at 37° C. At various time intervals (0 to 4 hrs), cell pellets were collected after centrifugation at 13,000×g for 1 min, washed with PBS and extracted with ice-cold 0.2 M perchloric acid. The acid extracts were clarified by centrifugation, neutralized with KOH, centrifuged to remove insoluble potassium perchlorate, evaporated to dryness under reduced pressure (Buchler Evapo-Mix apparatus) and constituted with 200 μl of methanol (Zimmerman et al., *J. Biol. Chem.* 262:5748, 1987). The samples were analyzed for AZT (open bar) and DP-AZT (solid bar) by a HPLC system (Beckman-Model 340) equipped with an on-line Flow-One beta radioactive flow detector (Model CR, 2.5 ml flow cell Radiomatic Instruments), using reverse phase Econosphere C18 column (150×4.6 mm, 5 μ) with 50% methanol as the mobile phase. Retention times for AZT and DP-AZT at a flow rate of 1 ml/min were 2.7 and 9 min respectively. These results are shown in FIG. 3A.

6.2.3. HYDROLYSIS OF DP-AZT IN MOUSE BONE MARROW CELLS

Figure 3B:
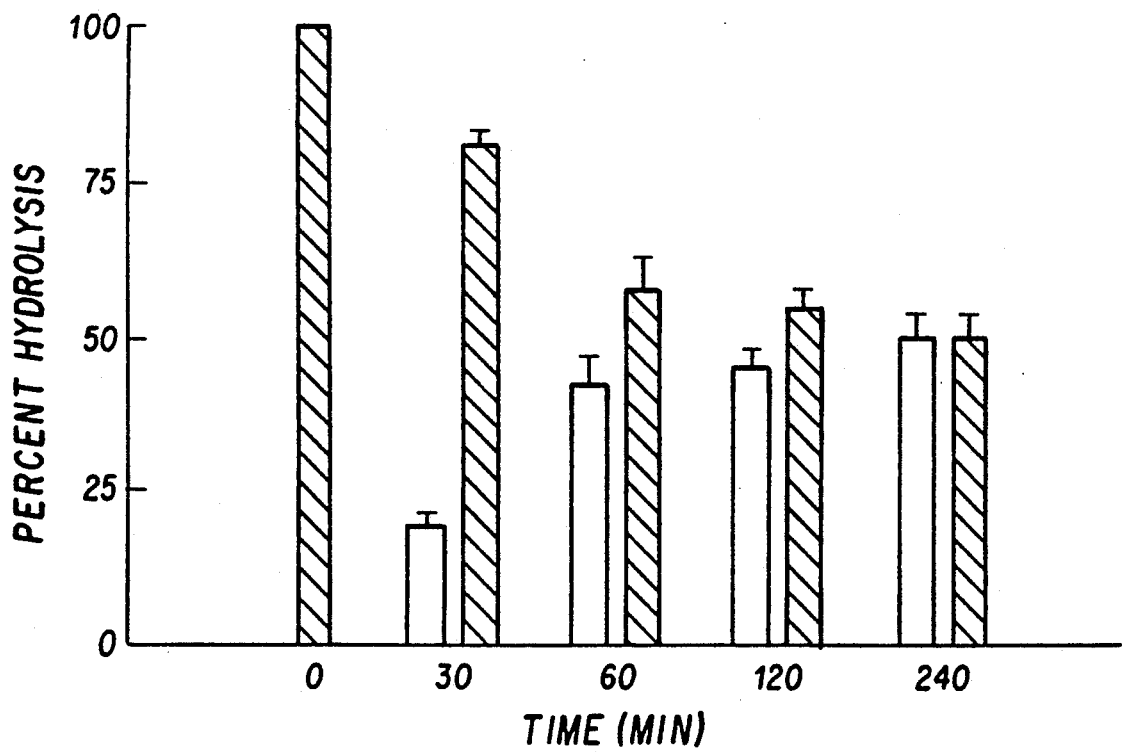

Bone marrow cells were obtained from femurs of 8-week old CD-1 mice. The femurs were removed aseptically and rinsed in RPMI-1640. Bone marrow cells were flushed with medium by using a 19-gauge needle and a single cell suspension was made by pipette action. These cells were used for hydrolytic experiments similar to described above for PBL. These results are shown in FIG. 3B.

To 900 μl of rat liver microsomes containing 15.5 mg protein/ml (Wong et al., *Biochem. Pharmacol.* 37:473, 1988), 100 μl of DP-AZT (2 mg/ml dissolved in dimethylsulfoxide) was added and incubated at 37° C. in a water bath. At various time intervals (0 to 4 h) 100 μl of sample was withdrawn and added immediately to ice-cold methanol (400 μl). The samples were centrifuged and supernatants were filtered through nylon-66 filters (0.45 μm) and analyzed as described previously except that AZT (open bar) and DP-AZT (solid bar) were detected by a variable wavelength UV detector (Beckman Model 165) at 267 nm with a peak retention time of 2.7 and 9 min respectively, at a flow rate of 1 ml/min. These results are shown in FIG. 3.

6.2.4. TOXICITY OF BONE MARROW CELLS

Figure 4:
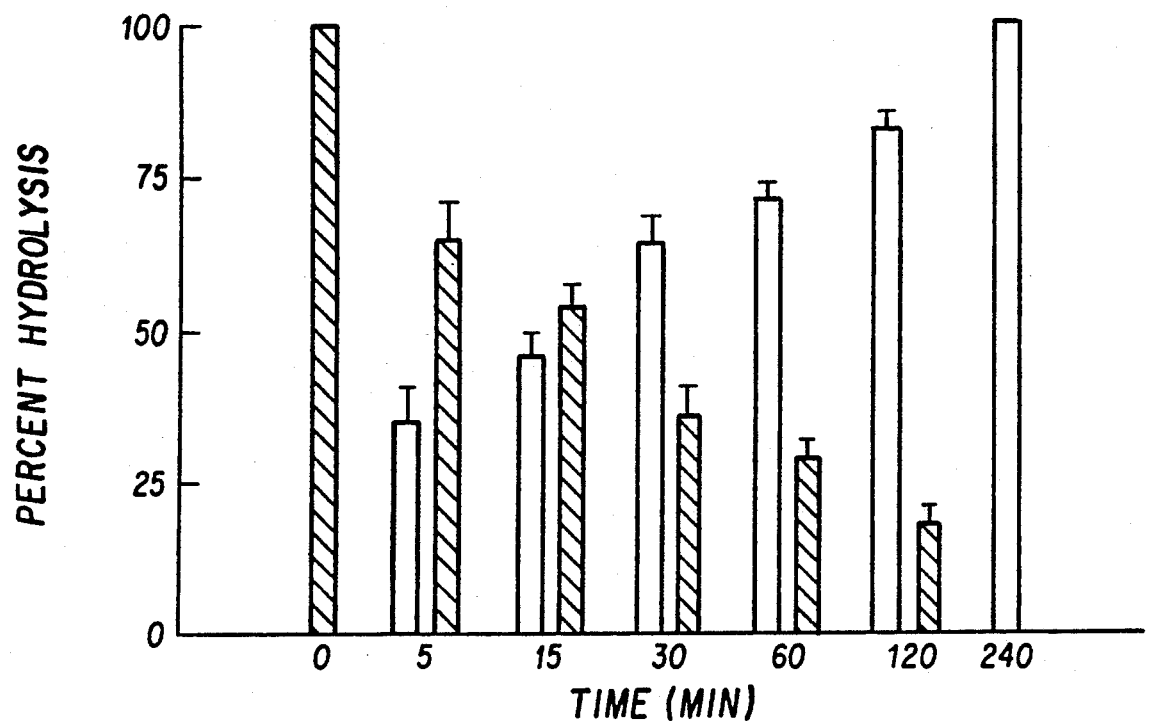
FIG. 4 shows the pattern of hydrolysis of DP-AZT by rat liver microsomes.

The bone marrow cells were obtained from CD-1 mice as described under Section 6.2.3, supra. Approximately $2 \times 10^5$ cells in 100 μl of medium were plated in a 96-well plate, 100 μl of drug solution at various concentrations (0–500 μM) was added, and the plate was incubated at 37° C. for 60 hr. [$^3$H]-Thymidine (0.2 μc/well, specific activity 30 c/mmole) was pulsed for 12 hr, and at the end of 72 hr cells were harvested by using Skatron 7019 cell harvester. Filter papers were counted for radioactivity and the percent inhibition of incorporation of [H]-thymidine was calculated for each concentration of AZT (open bar) and DP-AZT (solid bar). These results are shown in FIG. 4 (*$p<0.005$ is determined by student's t test compared to AZT.

6.2.5. ANTIVIRAL ACTIVITY

Inhibition of HIV-1 replication was determined using PBL from seronegative donors. PBL activated with 2 μg/ml PHA for 72 hrs were washed with medium and $10 \times 10^6$ cells were incubated for 4 hr at 37° C. (Mitsuya et al., *PNAS USA* 82:7096, 1988) in 5 ml medium containing the appropriate concentration of the drug. The cells were then infected with $10^4$ TCID$_{50}$ of HIV (isolated CD 451) by the addition of 0.1 ml of virus preparation and gentle rocking of the cultures of 15 min intervals for 90 min at room temperature. The fluid volume was increased to 10ml and the cultures maintained at 37° C. in a humidified 5% $CO_2$-in-air atmosphere. On day 3 post-infection, half the cell-free fluid in each culture was removed and replaced with fresh medium containing the respective drug. The extent of HIV replication in a control and the experimental cultures was evaluated 7 days post-infection by quantifying the concentration of HIV-specific p24 antigen in an undiluted and 5-fold serial dilutions of the culture supernatants using commercial antigen-capture assay kits (DuPont, Billerica, Mass.). The concentration of HIV-specific p24 antigen in the 7 day supernatant fluid of a drug-free control culture was 372,835 pg/ml.

TABLE I

| Drug Concentration (μM) | AZT pg/ml | AZT % reduction of control | DP-AZT pg/ml | DP-AZT % reduction of control |
|---|---|---|---|---|
| 10.0 | 2,235 | 99.4 | 215 | 99.9 |
| 5.0 | 1,758 | 99.5 | 475 | 99.9 |
| 0.5 | 67,273 | 82.0 | 3,310 | 99.1 |

What is claimed is:

1. A compound having the formula

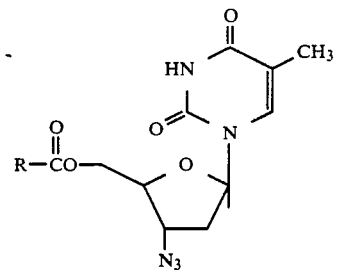

wherein R is selected from the group consisting of

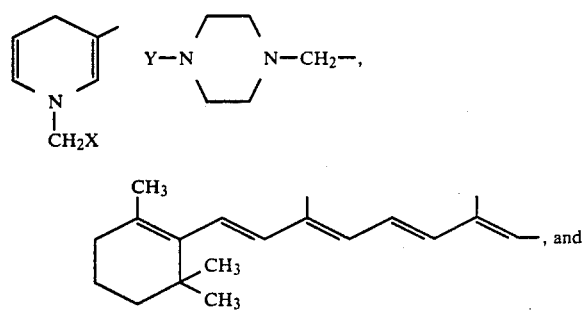

an amino acid residue;
wherein X is hydrogen, carboxyl, $C_1$-$C_6$ alkyl or benzyl, and Y is $C_1$-$C_6$ alkyl or $C_6$-$C_{10}$ aryl.

2. The compound of claim 1 having the formula:

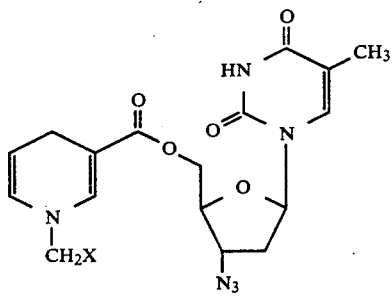

wherein X is hydrogen, carboxyl, $C_1-C_6$ alkyl or benzyl.

3. The compound of claim 2 wherein X is hydrogen.

4. The compound of claim 1 having the formula

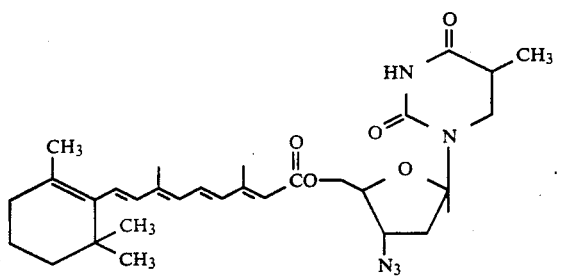

5. The compound of claim 1 having the formula

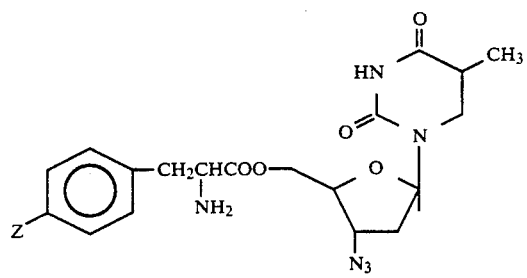

where Z is H or OH.

6. The compound of claim 1 having the formula

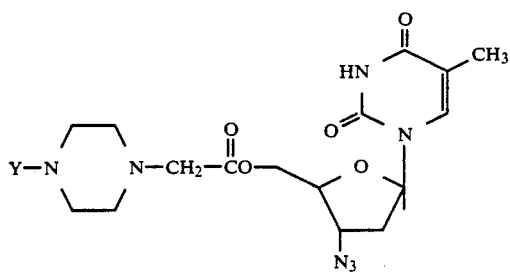

wherein Y is phenyl, methyl or H.

7. A pharmaceutical composition useful for treatment of retroviral infection which comprises an effective amount of a compound of claim 1 in combination with a pharmaceutically acceptable carrier.

8. A pharmaceutical composition useful for treatment of retroviral infection which comprises an effective amount of compound of claim 3 in combination with a pharmaceutically acceptable carrier.

9. A pharmaceutical composition useful for treatment of retroviral infection which comprises an effective amount of a compound of claim 4 in combination with a pharmaceutically acceptable carrier.

10. A pharmaceutical composition useful for treatment of retroviral infection which comprises an effective amount of a compound of claim 5 in combination with a pharmaceutically acceptable carrier.

11. A pharmaceutical composition useful for treatment of retroviral infection which comprises an effective amount of a compound of claim 6 in combination with a pharmaceutically acceptable carrier.

12. The composition of claim 7 in unit dosage form.
13. The composition of claim 8 in unit dosage form.
14. The composition of claim 9 in unit dosage form.
15. The composition of claim 10 in unit dosage form.
16. The composition of claim 11 in unit dosage form.
17. The composition of claim 12 or 13 or 14 or 15 or 16 for oral administration which comprises from 150-250 mg of the compound.
18. The composition of claim 12 or 13 or 14 or 15 or 16 for parenteral administration which comprises about 100-200 μg of the compound.

19. A method for treatment of retroviral infection which comprises administering to an individual in need of such treatment an effective amount of a compound having the formula:

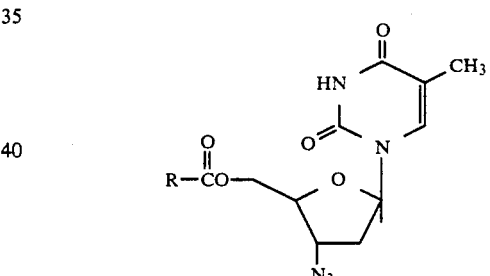

wherein R is selected from the group consisting of

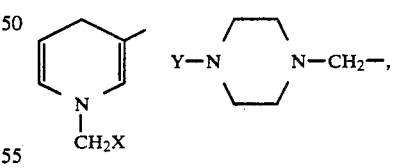

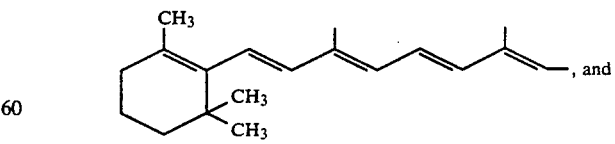

an amino acid residue;
and wherein X is hydrogen, carboxyl, $C_1-C_6$ alkyl or benzyl, and Y is $C_1-C_6$ alkyl or $C_6-C_{10}$ aryl.

20. The method of claim 19 wherein the compound has the formula:

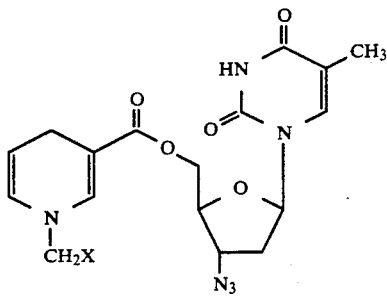

wherein X is hydrogen, carboxyl, $C_1$-$C_6$ alkyl, hydroxy,

21. The method of claim 20 wherein, in the compound, X is hydrogen.

22. The method of claim 19 wherein the compound has the formula:

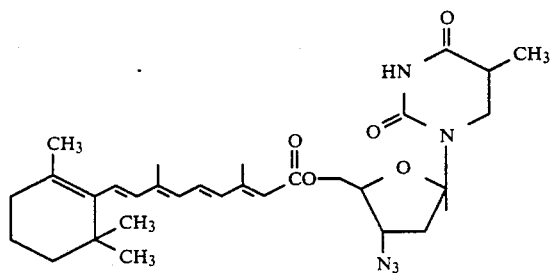

23. The method of claim 19 wherein the compound has the formula:

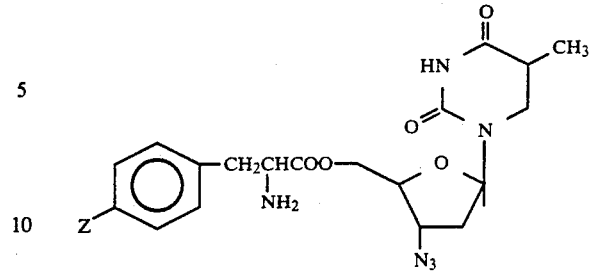

wherein Z is H or OH.

24. The method of claim 19 wherein the compound has the formula:

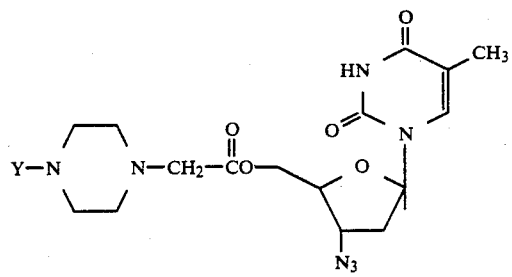

wherein Y is phenyl.

25. The method of claim 19 or 20 or 21 or 22 or 23 or 24 wherein the infection is caused by HIV-1.

26. The method of claim 24 wherein the compound is administered orally in an amount of about 150-250 mg at a frequency of about every 4 hours.

27. The method of claim 24 wherein the compound is administered parenterally in an amount of about 100-200 µg at a frequency of about every 4 hours.

28. A compound of the formula

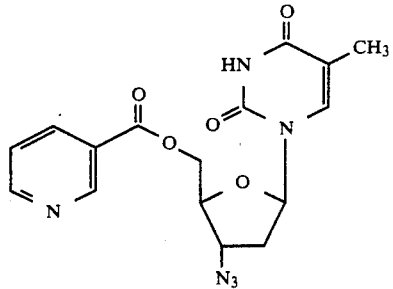

* * * * *

UNITED STATES PATENT AND TRADEMARK OFFICE
CERTIFICATE OF CORRECTION

PATENT NO. : 5,026,688

DATED : June 25, 1991

INVENTOR(S) : Krishna Agrawal

It is certified that error appears in the above-identified patent and that said Letters Patent is hereby corrected as shown below:

This subject invention was made with government support under Grant No. AI 25909. The government has certain rights in this invention.

Signed and Sealed this

Fourteenth Day of February, 1995

Attest:

BRUCE LEHMAN

Attesting Officer                Commissioner of Patents and Trademarks